United States Patent
Peyser

(10) Patent No.: US 7,801,582 B2
(45) Date of Patent: Sep. 21, 2010

(54) ANALYTE MONITORING AND MANAGEMENT SYSTEM AND METHODS THEREFOR

(75) Inventor: Thomas Peyser, Menlo Park, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 993 days.

(21) Appl. No.: 11/396,181

(22) Filed: Mar. 31, 2006

(65) Prior Publication Data

US 2009/0076359 A1 Mar. 19, 2009

(51) Int. Cl.
*A61B 5/05* (2006.01)
(52) U.S. Cl. .................. 600/345; 600/347; 600/365
(58) Field of Classification Search ............... 607/18; 604/65, 66; 600/365, 345, 300; 204/403.01–403.15, 204/406–407
See application file for complete search history.

(56) References Cited

U.S. PATENT DOCUMENTS

| | | | |
|---|---|---|---|
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,425,920 A | 1/1984 | Bourland et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,619,793 A | 10/1986 | Lee | |
| 4,671,288 A | 6/1987 | Gough | |
| 4,703,756 A | 11/1987 | Gough et al. | |
| 4,731,726 A | 3/1988 | Allen, III | |
| 4,749,985 A | 6/1988 | Corsberg | |
| 4,757,022 A | 7/1988 | Shults et al. | |
| 4,777,953 A | 10/1988 | Ash et al. | |

(Continued)

FOREIGN PATENT DOCUMENTS

EP  0098592  1/1984

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner*—Robert L Nasser
*Assistant Examiner*—Michael D'Angelo
(74) *Attorney, Agent, or Firm*—Jackson & Co., LLP

(57) ABSTRACT

Method and apparatus for providing multiple data receiver units in a data monitoring and management system such as analyte monitoring system where a first data receiver includes all of the functionalities for the data monitoring and management system receiver unit, and a second data receiver unit is configured with a limited functions to provide application specific convenience to the user or patient is disclosed.

21 Claims, 4 Drawing Sheets

U.S. PATENT DOCUMENTS

| | | | |
|---|---|---|---|
| 4,779,618 A | 10/1988 | Mund et al. | |
| 4,854,322 A | 8/1989 | Ash et al. | |
| 4,890,620 A | 1/1990 | Gough | |
| 4,895,147 A | 1/1990 | Bodicky et al. | |
| 4,925,268 A | 5/1990 | Iyer et al. | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,055,171 A | 10/1991 | Peck | |
| 5,082,550 A | 1/1992 | Rishpon et al. | |
| 5,106,365 A | 4/1992 | Hernandez | |
| 5,122,925 A | 6/1992 | Inpyn | |
| 5,165,407 A | 11/1992 | Wilson et al. | |
| 5,246,867 A | 9/1993 | Lakowicz et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,390,671 A | 2/1995 | Lord et al. | |
| 5,391,250 A | 2/1995 | Cheney, II et al. | |
| 5,408,999 A | 4/1995 | Singh et al. | |
| 5,411,647 A | 5/1995 | Johnson et al. | |
| 5,431,160 A | 7/1995 | Wilkins | |
| 5,431,921 A | 7/1995 | Thombre | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,586,553 A | 12/1996 | Halili et al. | |
| 5,593,852 A | 1/1997 | Heller et al. | |
| 5,601,435 A | 2/1997 | Quy | |
| 5,609,575 A | 3/1997 | Larson et al. | |
| 5,628,310 A | 5/1997 | Rao et al. | |
| 5,653,239 A | 8/1997 | Pompei et al. | |
| 5,665,222 A | 9/1997 | Heller et al. | |
| 5,711,001 A | 1/1998 | Bussan et al. | |
| 5,711,861 A | 1/1998 | Ward et al. | |
| 5,735,285 A | 4/1998 | Albert et al. | |
| 5,772,586 A | 6/1998 | Heinonen et al. | |
| 5,791,344 A | 8/1998 | Schulman et al. | |
| 5,899,855 A | 5/1999 | Brown | |
| 5,924,979 A * | 7/1999 | Swedlow et al. | 600/300 |
| 5,925,021 A | 7/1999 | Castellano et al. | |
| 5,942,979 A | 8/1999 | Luppino | |
| 5,957,854 A | 9/1999 | Besson et al. | |
| 5,961,451 A | 10/1999 | Reber et al. | |
| 5,964,993 A | 10/1999 | Blubaugh, Jr. et al. | |
| 5,965,380 A | 10/1999 | Heller et al. | |
| 5,971,922 A | 10/1999 | Arita et al. | |
| 5,995,860 A | 11/1999 | Sun et al. | |
| 6,001,067 A | 12/1999 | Shults et al. | |
| 6,024,699 A | 2/2000 | Surwit et al. | |
| 6,049,727 A | 4/2000 | Crothall | |
| 6,083,710 A | 7/2000 | Heller et al. | |
| 6,088,608 A | 7/2000 | Schulman et al. | |
| 6,091,976 A | 7/2000 | Pfeiffer et al. | |
| 6,093,172 A | 7/2000 | Funderburk et al. | |
| 6,103,033 A | 8/2000 | Say et al. | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,134,461 A | 10/2000 | Say et al. | |
| 6,159,147 A | 12/2000 | Lichter et al. | |
| 6,162,611 A | 12/2000 | Heller et al. | |
| 6,175,752 B1 * | 1/2001 | Say et al. | 600/345 |
| 6,200,265 B1 | 3/2001 | Walsh et al. | |
| 6,212,416 B1 | 4/2001 | Ward et al. | |
| 6,219,574 B1 | 4/2001 | Cormier et al. | |
| 6,248,067 B1 | 6/2001 | Causey, III et al. | |
| 6,275,717 B1 | 8/2001 | Gross et al. | |
| 6,283,761 B1 | 9/2001 | Joao | |
| 6,284,478 B1 | 9/2001 | Heller et al. | |
| 6,293,925 B1 | 9/2001 | Safabash et al. | |
| 6,295,506 B1 | 9/2001 | Heinonen et al. | |
| 6,306,104 B1 | 10/2001 | Cunningham et al. | |
| 6,309,884 B1 | 10/2001 | Cooper et al. | |
| 6,329,161 B1 | 12/2001 | Heller et al. | |
| 6,348,640 B1 | 2/2002 | Navot et al. | |
| 6,359,444 B1 | 3/2002 | Grimes | |
| 6,360,888 B1 | 3/2002 | McIvor et al. | |
| 6,366,794 B1 | 4/2002 | Moussy et al. | |
| 6,377,828 B1 | 4/2002 | Chaiken et al. | |
| 6,379,301 B1 | 4/2002 | Worthington et al. | |
| 6,424,847 B1 | 7/2002 | Mastrototaro et al. | |
| 6,427,088 B1 | 7/2002 | Bowman, IV et al. | |
| 6,440,068 B1 | 8/2002 | Brown et al. | |
| 6,478,736 B1 | 11/2002 | Mault | |
| 6,484,046 B1 | 11/2002 | Say et al. | |
| 6,514,718 B2 | 2/2003 | Heller et al. | |
| 6,522,927 B1 | 2/2003 | Bishay et al. | |
| 6,551,494 B1 | 4/2003 | Heller et al. | |
| 6,558,320 B1 * | 5/2003 | Causey et al. | 600/300 |
| 6,558,321 B1 | 5/2003 | Burd et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,564,105 B2 | 5/2003 | Starkweather et al. | |
| 6,565,509 B1 | 5/2003 | Say et al. | |
| 6,571,128 B2 | 5/2003 | Lebel et al. | |
| 6,576,101 B1 | 6/2003 | Heller et al. | |
| 6,577,899 B2 | 6/2003 | Lebel et al. | |
| 6,579,690 B1 | 6/2003 | Bonnecaze et al. | |
| 6,585,644 B2 | 7/2003 | Lebel et al. | |
| 6,591,125 B1 | 7/2003 | Buse et al. | |
| 6,595,919 B2 | 7/2003 | Berner et al. | |
| 6,605,200 B1 | 8/2003 | Mao et al. | |
| 6,605,201 B1 | 8/2003 | Mao et al. | |
| 6,607,509 B2 | 8/2003 | Bobroff et al. | |
| 6,610,012 B2 | 8/2003 | Mault | |
| 6,633,772 B2 | 10/2003 | Ford et al. | |
| 6,635,014 B2 | 10/2003 | Starkweather et al. | |
| 6,648,821 B2 | 11/2003 | Lebel et al. | |
| 6,654,625 B1 | 11/2003 | Say et al. | |
| 6,659,948 B2 | 12/2003 | Lebel et al. | |
| 6,668,196 B1 | 12/2003 | Villegas et al. | |
| 6,687,546 B2 | 2/2004 | Lebel et al. | |
| 6,689,056 B1 | 2/2004 | Kilcoyne et al. | |
| 6,694,191 B2 | 2/2004 | Starkweather et al. | |

| | | | | | | |
|---|---|---|---|---|---|---|
| 6,695,860 B1 | 2/2004 | Ward et al. | | 2002/0128594 A1 | 9/2002 | Das et al. |
| 6,702,857 B2 | 3/2004 | Brauker et al. | | 2002/0161288 A1 | 10/2002 | Shin et al. |
| 6,733,446 B2 | 5/2004 | Lebel et al. | | 2003/0023317 A1 | 1/2003 | Brauker et al. |
| 6,740,075 B2 | 5/2004 | Lebel et al. | | 2003/0023461 A1 | 1/2003 | Quintanilla et al. |
| 6,741,877 B1 | 5/2004 | Shults et al. | | 2003/0032867 A1 | 2/2003 | Crothall et al. |
| 6,746,582 B2 | 6/2004 | Heller et al. | | 2003/0032874 A1 | 2/2003 | Rhodes et al. |
| 6,758,810 B2 | 7/2004 | Lebel et al. | | 2003/0042137 A1 | 3/2003 | Mao et al. |
| 6,770,030 B1 | 8/2004 | Schaupp et al. | | 2003/0065308 A1 | 4/2003 | Lebel et al. |
| 6,790,178 B1 | 9/2004 | Mault et al. | | 2003/0134347 A1 | 7/2003 | Heller et al. |
| 6,809,653 B1 | 10/2004 | Mann et al. | | 2003/0144581 A1 * | 7/2003 | Conn et al. ................. 600/309 |
| 6,810,290 B2 | 10/2004 | Lebel et al. | | 2003/0168338 A1 | 9/2003 | Gao et al. |
| 6,811,533 B2 | 11/2004 | Lebel et al. | | 2003/0176933 A1 | 9/2003 | Lebel et al. |
| 6,811,534 B2 | 11/2004 | Bowman, IV et al. | | 2003/0187338 A1 | 10/2003 | Say et al. |
| 6,813,519 B2 | 11/2004 | Lebel et al. | | 2003/0199790 A1 | 10/2003 | Boecker et al. |
| 6,862,465 B2 | 3/2005 | Shults et al. | | 2003/0212379 A1 | 11/2003 | Bylund et al. |
| 6,873,268 B2 | 3/2005 | Lebel et al. | | 2003/0217966 A1 | 11/2003 | Tapsak et al. |
| 6,881,551 B2 | 4/2005 | Heller et al. | | 2004/0010207 A1 | 1/2004 | Flaherty et al. |
| 6,892,085 B2 | 5/2005 | McIvor et al. | | 2004/0011671 A1 | 1/2004 | Shults et al. |
| 6,895,265 B2 | 5/2005 | Silver | | 2004/0040840 A1 | 3/2004 | Mao et al. |
| 6,931,327 B2 | 8/2005 | Goode, Jr. et al. | | 2004/0045879 A1 | 3/2004 | Shults et al. |
| 6,932,894 B2 | 8/2005 | Mao et al. | | 2004/0054263 A1 | 3/2004 | Moerman et al. |
| 6,936,006 B2 | 8/2005 | Sabra | | 2004/0064068 A1 | 4/2004 | DeNuzzio et al. |
| 6,942,518 B2 | 9/2005 | Liamos et al. | | 2004/0106858 A1 | 6/2004 | Say et al. |
| 6,950,708 B2 | 9/2005 | Bowman, IV et al. | | 2004/0122353 A1 | 6/2004 | Shahmirian et al. |
| 6,958,705 B2 | 10/2005 | Lebel et al. | | 2004/0122489 A1 * | 6/2004 | Mazar et al. ................. 607/60 |
| 6,968,294 B2 | 11/2005 | Gutta et al. | | 2004/0133164 A1 | 7/2004 | Funderburk et al. |
| 6,971,274 B2 | 12/2005 | Olin | | 2004/0135684 A1 | 7/2004 | Steinthal et al. |
| 6,974,437 B2 | 12/2005 | Lebel et al. | | 2004/0138588 A1 | 7/2004 | Saikley et al. |
| 6,990,366 B2 | 1/2006 | Say et al. | | 2004/0152622 A1 | 8/2004 | Keith et al. |
| 6,997,907 B2 | 2/2006 | Safabash et al. | | 2004/0167801 A1 | 8/2004 | Say et al. |
| 6,998,247 B2 | 2/2006 | Monfre et al. | | 2004/0171921 A1 | 9/2004 | Say et al. |
| 7,003,336 B2 | 2/2006 | Holker et al. | | 2004/0176672 A1 | 9/2004 | Silver et al. |
| 7,003,340 B2 | 2/2006 | Say et al. | | 2004/0186362 A1 | 9/2004 | Brauker et al. |
| 7,003,341 B2 | 2/2006 | Say et al. | | 2004/0186365 A1 | 9/2004 | Jin et al. |
| 7,024,245 B2 | 4/2006 | Lebel et al. | | 2004/0193090 A1 | 9/2004 | Lebel et al. |
| 7,025,743 B2 * | 4/2006 | Mann et al. ................. 604/66 | | 2004/0199059 A1 | 10/2004 | Brauker et al. |
| 7,041,068 B2 | 5/2006 | Freeman et al. | | 2004/0204687 A1 | 10/2004 | Mogensen et al. |
| 7,041,468 B2 | 5/2006 | Drucker et al. | | 2004/0225338 A1 | 11/2004 | Lebel et al. |
| 7,052,483 B2 | 5/2006 | Wojcik | | 2004/0236200 A1 | 11/2004 | Say et al. |
| 7,056,302 B2 | 6/2006 | Douglas | | 2004/0254433 A1 | 12/2004 | Bandis et al. |
| 7,074,307 B2 | 7/2006 | Simpson et al. | | 2004/0254434 A1 | 12/2004 | Goodnow et al. |
| 7,081,195 B2 | 7/2006 | Simpson et al. | | 2004/0267300 A1 | 12/2004 | Mace |
| 7,098,803 B2 | 8/2006 | Mann et al. | | 2005/0003470 A1 | 1/2005 | Nelson et al. |
| 7,108,778 B2 | 9/2006 | Simpson et al. | | 2005/0004494 A1 | 1/2005 | Perez et al. |
| 7,110,803 B2 | 9/2006 | Shults et al. | | 2005/0010269 A1 | 1/2005 | Lebel et al. |
| 7,113,821 B1 | 9/2006 | Sun et al. | | 2005/0027177 A1 | 2/2005 | Shin et al. |
| 7,134,999 B2 | 11/2006 | Brauker et al. | | 2005/0031689 A1 | 2/2005 | Shults et al. |
| 7,136,689 B2 | 11/2006 | Shults et al. | | 2005/0043598 A1 | 2/2005 | Goode, Jr. et al. |
| 7,171,274 B2 | 1/2007 | Starkweather et al. | | 2005/0070819 A1 | 3/2005 | Poux et al. |
| 7,190,988 B2 | 3/2007 | Say et al. | | 2005/0090607 A1 | 4/2005 | Tapsak et al. |
| 7,192,450 B2 | 3/2007 | Brauker et al. | | 2005/0112169 A1 | 5/2005 | Brauker et al. |
| 7,198,606 B2 | 4/2007 | Boecker et al. | | 2005/0114068 A1 | 5/2005 | Chey et al. |
| 7,226,978 B2 | 6/2007 | Tapsak et al. | | 2005/0121322 A1 | 6/2005 | Say et al. |
| 7,276,029 B2 | 10/2007 | Goode, Jr. et al. | | 2005/0131346 A1 | 6/2005 | Douglas |
| 7,278,983 B2 | 10/2007 | Ireland et al. | | 2005/0143635 A1 | 6/2005 | Kamath et al. |
| 7,299,082 B2 | 11/2007 | Feldman et al. | | 2005/0176136 A1 | 8/2005 | Burd et al. |
| 7,310,544 B2 | 12/2007 | Brister et al. | | 2005/0182306 A1 * | 8/2005 | Sloan ........................ 600/300 |
| 7,335,294 B2 | 2/2008 | Heller et al. | | 2005/0187720 A1 | 8/2005 | Goode, Jr. et al. |
| 7,340,309 B2 | 3/2008 | Miazga et al. | | 2005/0192557 A1 | 9/2005 | Brauker et al. |
| 7,364,592 B2 | 4/2008 | Carr-Brendel et al. | | 2005/0195930 A1 | 9/2005 | Spital et al. |
| 7,366,556 B2 | 4/2008 | Brister et al. | | 2005/0199494 A1 | 9/2005 | Say et al. |
| 7,379,765 B2 | 5/2008 | Petisce et al. | | 2005/0203360 A1 | 9/2005 | Brauker et al. |
| 7,424,318 B2 | 9/2008 | Brister et al. | | 2005/0222518 A1 | 10/2005 | Dib |
| 7,460,898 B2 | 12/2008 | Brister et al. | | 2005/0239154 A1 | 10/2005 | Feldman et al. |
| 7,467,003 B2 | 12/2008 | Brister et al. | | 2005/0239156 A1 | 10/2005 | Drucker et al. |
| 7,471,972 B2 | 12/2008 | Rhodes et al. | | 2005/0241957 A1 | 11/2005 | Mao et al. |
| 7,494,465 B2 | 2/2009 | Brister et al. | | 2005/0245795 A1 | 11/2005 | Goode, Jr. et al. |
| 7,497,827 B2 | 3/2009 | Brister et al. | | 2005/0245799 A1 | 11/2005 | Brauker et al. |
| 2002/0019022 A1 | 2/2002 | Dunn et al. | | 2005/0277164 A1 | 12/2005 | Drucker et al. |
| 2002/0022855 A1 | 2/2002 | Bobroff et al. | | 2005/0287620 A1 | 12/2005 | Heller et al. |
| 2002/0042090 A1 | 4/2002 | Heller et al. | | 2006/0001538 A1 | 1/2006 | Kraft et al. |
| 2002/0103499 A1 | 8/2002 | Perez et al. | | 2006/0010098 A1 | 1/2006 | Goodnow et al. |
| 2002/0106709 A1 | 8/2002 | Potts et al. | | 2006/0015020 A1 | 1/2006 | Neale et al. |

| | | |
|---|---|---|
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0166629 A1 | 7/2006 | Reggiardo |
| 2006/0173444 A1 | 8/2006 | Choy et al. |
| 2006/0189863 A1 | 8/2006 | Heller et al. |
| 2006/0200970 A1 | 9/2006 | Brister et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0258929 A1 * | 11/2006 | Goode et al. ................ 600/345 |
| 2007/0027381 A1 | 2/2007 | Stafford |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0106135 A1 | 5/2007 | Sloan et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0235331 A1 | 10/2007 | Simpson et al. |
| 2007/0249922 A1 | 10/2007 | Peyser et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0039702 A1 | 2/2008 | Hayter et al. |
| 2008/0045824 A1 | 2/2008 | Tapsak et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0108942 A1 | 5/2008 | Brister et al. |
| 2008/0114280 A1 | 5/2008 | Stafford |
| 2008/0119707 A1 | 5/2008 | Stafford |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/089103 | 9/2005 |
| WO | WO-2005/119524 | 12/2005 |
| WO | WO-2006/024671 | 3/2006 |
| WO | WO-2006/079114 | 7/2006 |
| WO | WO-2006/086423 | 8/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |

| WO | WO-2007/053832 | 12/2007 |
| WO | WO-2007/143225 | 12/2007 |
| WO | WO-2008/031106 | 3/2008 |
| WO | WO-2008/031110 | 3/2008 |
| WO | WO-2008/039944 | 4/2008 |
| WO | WO-2008/051920 | 5/2008 |
| WO | WO-2008/051924 | 5/2008 |
| WO | WO-2008/103620 | 8/2008 |
| WO | WO-2008/150917 | 12/2008 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.
Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.
Brooks, S. L., et al., "Development of an On-Line Glucose Sensor for Fermentation Monitoring", *Biosensors*, vol. 3, 1987/88, pp. 45-56.
Cass, A. E., et al., "Ferrocene-Medicated Enzyme Electrode for Amperometric Determination of Glucose", *Analytical Chemistry*, vol. 56, No. 4, 1984, 667-671.
Complaint, "*Abbott Diabetes Care, Inc. v. Dexcom, Inc.*", filed Aug. 11, 2005.
Complaint, Amended, "*Abbott Diabetes Care, Inc. v. Dexcom, Inc.*", filed Jun. 27, 2006.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Feldman, B., et al., "A Continuous Glucose Sensor Based on Wired Enzyme™ Technology-Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.

\* cited by examiner

ANALYTE MONITORING AND MANAGEMENT SYSTEM AND METHODS THEREFOR

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another portion of segment of the analyte sensor that is in communication with the transmitter unit. The transmitter unit is configured to transmit the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels.

The receiver/monitor units generally include sophisticated functionalities and features, while providing robust data management system, also provide a steep learning curve and challenge to the initial users of such devices. In addition, due to its sophistication and robust functionality, the reduction in the size of the receiver/monitor unit can be limited. For diabetic children that use the analyte monitoring system, for example, having a complex device such as the receiver/monitor unit may pose a health risk in addition to its intended benefit. Indeed, the receiver/monitor unit may be misprogrammed, or otherwise, its settings and/or features modified by the user and thus not operate properly.

In addition, due to its size, it is cumbersome to engage in physical activities such as exercise while carrying the receiver/monitor unit so as to be in signal range with the on-body transmitter unit.

In view of the foregoing, it would be desirable to have a system which includes a receiver/monitor unit for use with the data monitoring and management system which is compact in size and that has limited set of primary features that is less cumbersome to transport and which is easy to manipulate and use by children, for example.

SUMMARY OF THE INVENTION

In view of the foregoing, in accordance with the various embodiments of the present invention, there is provided a method and system for providing a secondary receiver/monitor unit in a data monitoring and management system which is configured for data communication with the primary receiver/monitor unit, and further, where the secondary receiver/monitor unit can replace the functionalities of the primary receiver/monitor unit during a predetermined time periods such as exercise periods, sleeping periods, travel periods, or any other periods during which access to the full functionality of the primary receiver/monitor unit is not needed.

These and other objects, features and advantages of the present invention will become more fully apparent from the following detailed description of the embodiments, the appended claims and the accompanying drawings.

DETAILED DESCRIPTION

Figure 1:
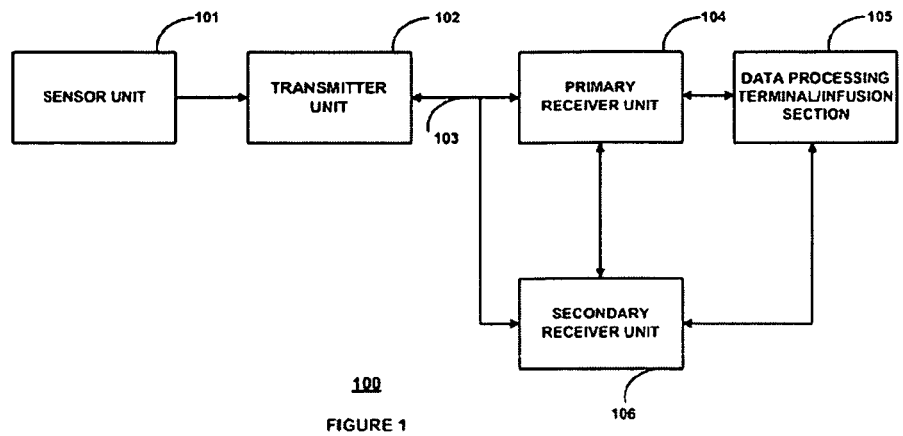
FIG. 1 illustrates a block diagram of a data monitoring and management system for practicing one embodiment of the present invention.

FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal in one embodiment may be configured to receive data directly from the transmitter unit 102 via a communication link 103 which may optionally be configured for bi-directional communication.

Also shown in FIG. 1 is a secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present invention, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 103, where the communication link 103, as described above, may be configured for bi-directional communication.

In this embodiment, the data processing terminal 105 which may include an insulin pump, may be configured to receive the analyte signals from the transmitter unit 102, and thus, incorporate the functions of the receiver 103 including data processing for managing the patient's insulin therapy and analyte monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Figure 2:
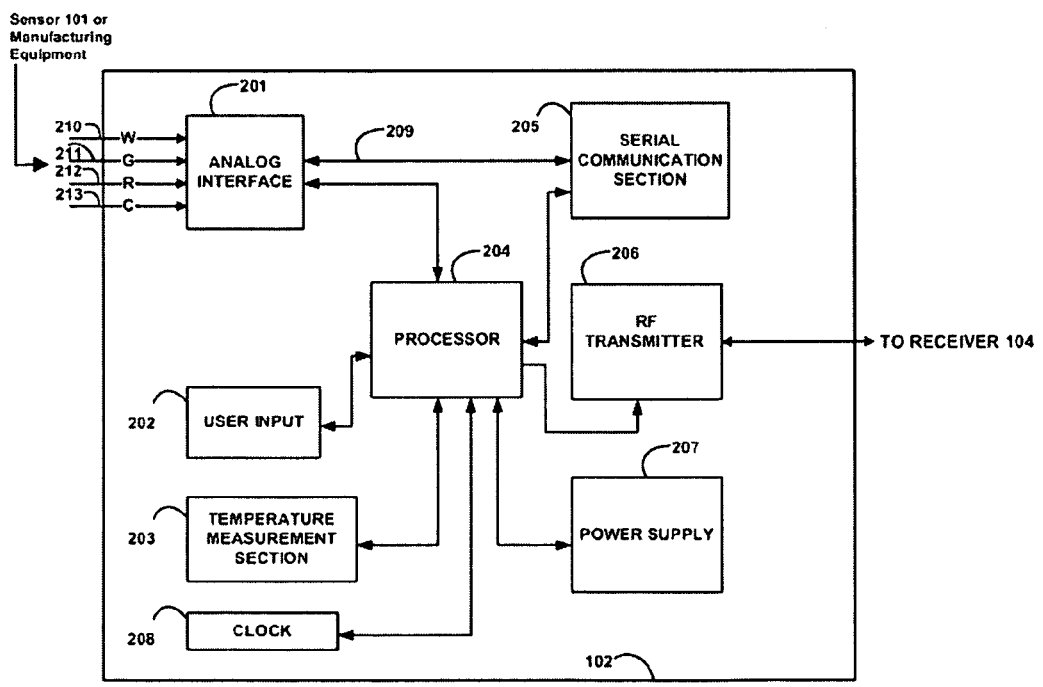
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter unit 102 for connection to the sensor unit 201 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard electrode (G) 211 and the processor 204 in the transmitter unit 102 of the data monitoring and management system 100. The leak detection circuit 214 in accordance with one embodiment of the present invention may be configured to detect leakage current in the sensor 101 to determine whether the measured sensor data are corrupt or whether the measured data from the sensor 101 is accurate.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application, and the disclosures of each of which are incorporated herein by reference for all purposes.

Figure 3:
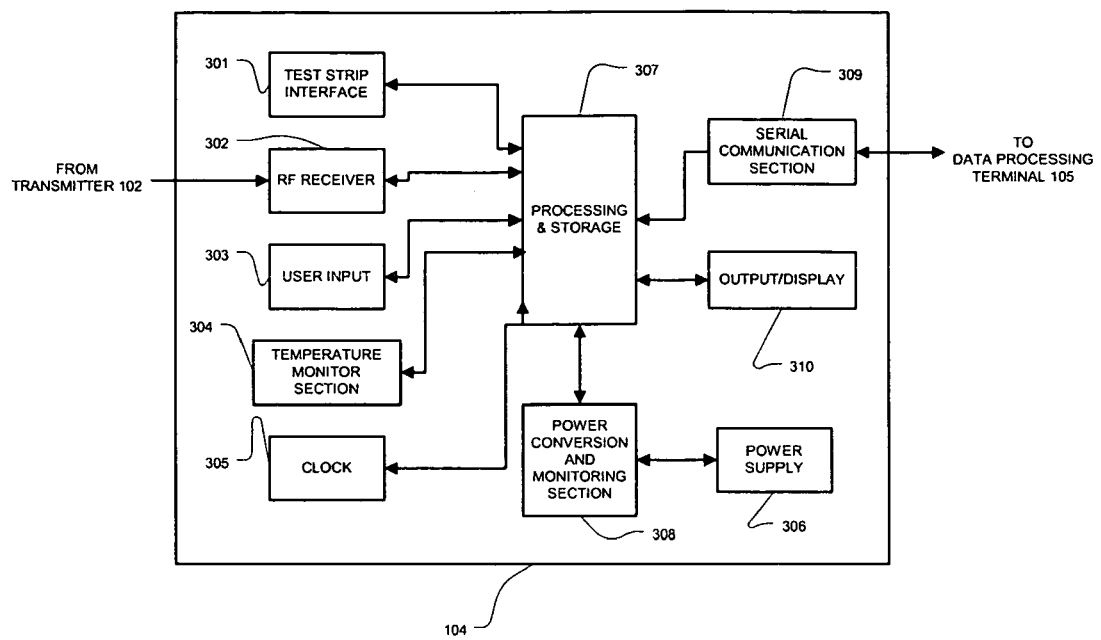
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the primary receiver unit 104 includes a blood glucose test strip interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307.

Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 104 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 is further configured to perform Manchester decoding as well as error detection and correction upon the encoded data signals received from the transmitter unit 102 via the communication link 103.

Referring back to FIGS. 1 and 3, in one embodiment of the present invention, the secondary receiver unit 106 may be configured substantially in the manner described in conjunction with FIG. 3. Alternatively, in another embodiment of the present invention, the secondary receiver unit 106 may be configured to include a limited number of functionalities as compared with the primary receiver unit 104 described in detail in conjunction with FIG. 3.

For example, in one embodiment of the present invention, the secondary receiver unit 106 maybe substantially incorporated into a wrist watch worn by the user of the analyte monitoring system. Accordingly, in addition to keeping accurate time, the secondary receiver unit 106 is configured to receive the transmitted signals from the transmitter unit 102 worn by the user. In one embodiment, the wrist watch/secondary receiver unit 106 configuration includes a display section that, in addition to displaying the time and date information, displays the monitored analyte levels substantially in real time received from the transmitter unit 102. This configuration is also programmable to store the received analyte data from the transmitter unit 102 which can later be transferred to the primary receiver unit 102. Other features of the receiver unit display such as trend information or graphical representation of the trend data, may not be displayed in this configuration given the limited display area size on the wrist watch.

In one embodiment, the communication link between the primary receiver unit 104 and the secondary receiver unit 106 may be established using Bluetooth communication protocol, and each device is configured to periodically transmit data such that the information stored in the primary receiver unit 104 and the secondary receiver unit 106 are maintained substantially up to date and in synchronization with each other. In addition, each of the primary receiver unit 104 and the secondary receiver unit 106 maybe configured to uniquely identify the transmitter unit 102 such that both primary receiver unit 104 and the secondary receiver unit 106 are configured to receive data transmission from the transmitter unit 102 without interruption, and to store the same in the respective storage sections of the receiver units.

In this manner, in one embodiment of the present invention, the user or patient may conveniently interchange the use between the primary receiver unit 104 and the secondary receiver unit 106 without any interruption in the analyte monitoring system 100, and importantly, without losing data transmitted from the transmitter unit 102. For example, a diabetic child using the analyte monitoring system 100 may carry the primary receiver unit 104 in her backpack during the course of the day, and wear the secondary receiver unit 106 which is configured as a wrist watch. During the time period when the backpack containing the primary receiver unit 104 is in close proximity to the transmitter unit 102 attached to the body of the diabetic child, the primary receiver unit 104 is configured to receive the transmitted data from the transmitter unit 102 corresponding to the monitored analyte levels of the diabetic child. During recess at school or any other time period during which the backpack containing the primary receiver unit 104 is not in signal range of the transmitter unit 102, the secondary receiver unit 106 is configured to receive the signals from the transmitter unit 104. Periodically during the day or at a preprogrammed time during a 24 hour period, the primary receiver unit 104 may be configured to synchronize with the secondary receiver unit 106 such that all of the transmitted signals from the transmitter unit 102 are stored in the primary receiver unit 104.

Such multiple receiver unit implementation of the analyte monitoring system may be additionally beneficial in other circumstances. For example, the secondary receiver unit 106 may be used during the time period that the user or patient is engaged in physical activities such as sports or other types of activities where carrying an electronic device such as the primary receiver unit 104 may be cumbersome.

In addition, the secondary receiver unit 106 may be configured to operate in a low power transmission state such as that complying with Class B transmission regulated by the Federal Aviation Authority (FAA) which mandate electronic transmission devices to be turned off during airplane take off and landing procedures. In such cases, the primary receiver unit 104 may be powered down completely while the Class-B compliant secondary receiver unit 106 maybe configured to continue receiving the signals from the transmitter unit 102. Thereafter, at a later time period when the primary receiver unit 104 may be turned on, the primary receiver unit 104 is configured to synchronize data with the secondary receiver unit 106 so that the transmitted signals from the transmitter unit 102 during the time that the primary receiver unit 104 was turned off can be captured and stored in the primary receiver unit 104.

Figure 4:
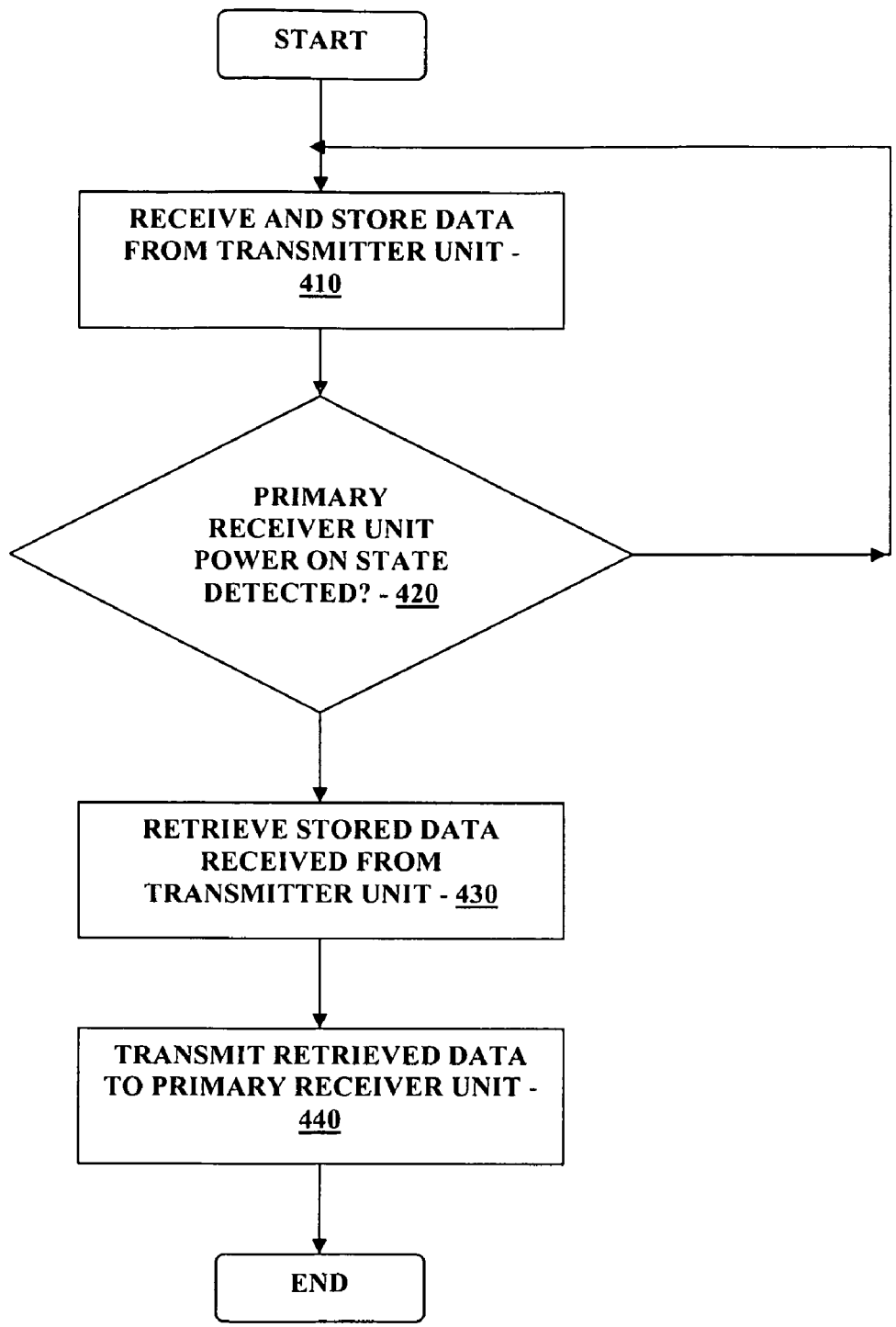
FIG. 4 is a flowchart illustrating data synchronization procedure between the primary receiver unit and the secondary receiver unit of the analyte monitoring system in accordance with one embodiment of the present invention.

FIG. 4 is a flowchart illustrating data synchronization procedure between the primary receiver unit and the secondary receiver unit of the analyte monitoring system in accordance with one embodiment of the present invention. Referring to FIG. 4, at step 410 in one embodiment of the present invention, the secondary receiver unit 106 (FIG. 1) is configured to receive and store the signals received from the transmitter unit 102 that are associated with the monitored analyte levels. Thereafter at step 420, the secondary receiver unit 106 determined whether the primary receiver unit 104 is back in the power on state. In one embodiment, the primary receiver unit 104 may be configured to broadcast a power on state signal as soon as it is powered on. Alternatively, in another embodiment, the secondary receiver unit 106 is configured to periodically transmit a signal to the primary receiver unit 104, and when a return acknowledgement signal is received by the secondary receiver unit 106 as originating from the primary receiver unit 104, it is determined that the primary receiver unit 104 is in the powered on state.

Referring back to FIG. 4, if it is determined at step 420 that the primary receiver unit 104 is not in the power on state, then the secondary receiver unit 106 returns to step 410 where the transmitter unit 102 signals are continuously received and stored. If however it is determined at step 420 that the primary receiver unit 104 is in the power on state, then at step 430, the secondary receiver unit 106 is configured to retrieve the stored data received from the transmitter unit 102, and at step 440, the secondary receiver unit 106 is configured to transmit the retrieved data corresponding to data received from the transmitter unit 102 to the primary receiver unit 104. Thereafter, optionally, the secondary receiver unit 106 may be configured to enter a powered down or hibernate mode to conserve its power supply. In the hibernate mode, the secondary receiver unit 106 may be configured to not accept data transmitted from the transmitter unit 102.

In an alternate embodiment, the secondary receiver unit 106 may be configured to continue to receive the transmitted data from the transmitter unit 102 even when the primary receiver unit 104 is in the power on state and receiving data from the transmitter unit 102. In this manner, transmitter unit 102 data redundancy may be achieved.

Figure 5:
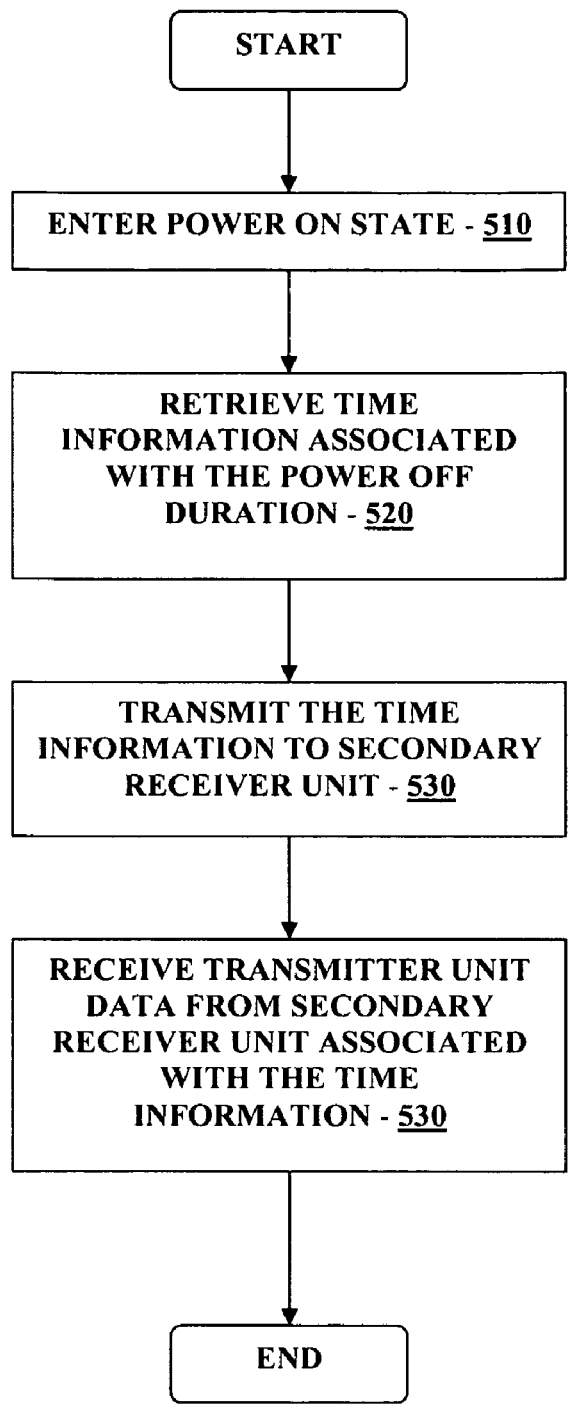
FIG. 5 is a flowchart illustrating data synchronization procedure between the primary receiver unit and the secondary receiver unit of the analyte monitoring system in accordance with another embodiment of the present invention.

FIG. 5 is a flowchart illustrating data synchronization procedure between the primary receiver unit and the secondary receiver unit of the analyte monitoring system in accordance with another embodiment of the present invention. Referring to FIG. 5, at step 510, the primary receiver unit 104 (FIG. 1) entered the power on state by, for example, the user or patient powering on the primary receiver unit 104. Thereafter at step 520, the primary receiver unit 520 is configured to retrieve the time information associated with the power off state duration. For example, in one embodiment, the primary receiver unit 104 is configured to retrieve the time stamp information (as maybe provided by its internal clock 305 (FIG. 3) of the beginning of the power off state, and the time stamp information of the beginning of the power on state.

Referring to FIG. 5, the retrieved time information associated with the power off duration is transmitted to the secondary receiver unit 106 at step 530. Thereafter, at step 540, the primary receiver unit 104 is configured to receive transmitter unit 102 data from the secondary receiver unit 104 that correspond to the time information associated with the power off duration. That is, since during the power off state the primary receiver unit 104 did not receive any data from the transmitter unit 102 which are associated with the monitored analyte level, the primary receiver unit 104 may be configured in one embodiment to receive this data from the secondary receiver unit 106.

In addition, within the scope of the present invention, the primary receiver unit 104 and the secondary receiver unit 106 may be configured as a bedside monitor system where, the secondary receiver unit 106 (or interchangeably the primary receiver unit 104) may be placed at or near the bedside of the child or patient wearing the transmitter unit 102. The primary receiver unit 104 (or interchangeably the secondary receiver unit 106) may be placed at another location within the house (or hospital or any other location within communication range with the secondary receiver unit 106. In this manner, even though the RF communication link 103 between the transmitter unit 102 and the remotely located primary receiver unit 104 may not be enabled due to distance, the secondary receiver unit 106 which is in signal communication with the transmitter unit 102 may be configured as a relay device to retransmit the received transmitter unit 102 signals to the primary receiver unit 104. In this manner, parents of diabetic children wearing a transmitter unit 102 to monitor the children's glucose levels, or patients in hospitals may conveniently and remotely monitor the analyte levels substantially in real time.

Accordingly, a system for providing analyte monitoring in one embodiment of the present invention includes a sensor configured for subcutaneous placement for detecting a plurality of analyte levels, a transmitter unit configured for electrical communication with the sensor; the transmitter unit configured to transmit a plurality of signals each associated with a respective one or more of the detected plurality of analyte levels, a first receiver unit configured to receive a first portion of the transmitted plurality of signals from the transmitter unit, a second receiver unit configured to receive a second portion of the transmitted signals from the transmitter unit.

In one embodiment, each of the plurality of signals transmitted by the transmitter unit maybe associated with a corresponding detection time information, where each detection time information may substantially correspond to the detection time of the corresponding associated analyte level by the sensor.

The second receiver unit maybe configured to transmit the received second portion of the signals to the first receiver unit, where the first portion of the plurality of signals and the second portion of the plurality of signals may be substantially non-overlapping.

Further, the first receiver unit may include a storage unit for storing the first and second portions of the plurality of the signals.

In addition, the first receiver unit may include an output unit for outputting one or more of a visual indication, an audible indication or a vibratory indication associated with the received one or more of the plurality of signals.

In a further aspect, the second receiver unit may include a housing substantially configured as one of a wrist watch, a bed side monitor unit, a two way radio communication unit, a mobile telephone, a pager, or a personal digital assistant.

The first receiver unit and the second receiver unit in yet another aspect may be configured to communicate over a communication link which may include one or more of an infrared communication link, an RF communication link, a Bluetooth communication link, or a cable connection.

In yet another aspect, each of the first and second receiver units may be configured for bi-directional communication.

A method of analyte monitoring in accordance with another embodiment of the present invention includes transmitting a plurality of signals associated with detected analyte levels, receiving a first portion of the plurality of signals at a first remote location, receiving a second portion of the plurality of signals at a second remote location, wherein the first and second portions of the plurality of signals are substantially non-overlapping.

The method may further include transmitting the second portion of the plurality of signals from the second remote location to the first remote location.

In another aspect, the method may also include one or more steps of storing the plurality of signals, or displaying at least a portion of the plurality of signals.

A method of analyte monitoring in accordance with still another embodiment of the present invention includes receiving one or more signals associated with a respective one or more analyte levels being monitored, storing the received one or more signals, detecting an active state of a receiver unit, and transmitting the stored one or more signals to the receiver unit.

In another aspect, the method may also include the steps of detecting the one or more analyte levels, and transmitting the one or more signals each corresponding to the detected one or more analyte levels substantially in real time.

A method of analyte monitoring in still yet another embodiment of the present invention includes retrieving a time information associated with an inactive state, transmitting the retrieved time information, and receiving one or more signals each associated with a monitored analyte level corresponding to the time information.

The time information may include a beginning time and an end time of the inactive state.

In a further aspect, the method may also include the storing the received one or more signals.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A system for providing analyte monitoring, comprising:
a sensor configured for subcutaneous placement for detecting a plurality of analyte levels;
a transmitter unit configured for electrical communication with the sensor; the transmitter unit configured to transmit a plurality of signals each associated with a respective one or more of the detected plurality of analyte levels;
a first receiver unit configured to receive a first portion of the transmitted plurality of signals from the transmitter unit; and
a second receiver unit configured to receive a second portion of the transmitted signals from the transmitter unit at least during an inactive state of the first receiver unit;
wherein the first receiver unit is further configured to provide time information associated with the inactive state.

2. The system of claim 1 wherein each of the plurality of signals transmitted by the transmitter unit is associated with a corresponding detection time information.

3. The system of claim 2 wherein each detection time information substantially corresponds to the detection time of the corresponding associated analyte level by the sensor.

4. The system of claim 1 wherein the second receiver unit is configured to transmit the received second portion of the signals to the first receiver unit.

5. The system of claim 4 wherein the first portion of the plurality of signals and the second portion of the plurality of signals are substantially non-overlapping.

6. The system of claim 4 wherein the first receiver unit includes a storage unit for storing the first and second portions of the plurality of the signals.

7. The system of claim 1 wherein the first receiver unit includes an output unit for outputting one or more of a visual indication, an audible indication or a vibratory indication associated with the received one or more of the plurality of signals.

8. The system of claim 1 wherein the second receiver unit includes a housing substantially configured as one of a wrist watch, a bed side monitor unit, a two way radio communication unit, a mobile telephone, a pager, or a personal digital assistant.

9. The system of claim 1 wherein the first receiver unit and the second receiver unit are configured to communicate over a communication link.

10. The system of claim 9 wherein the communication link includes one or more of an infrared communication link, an RF communication link, or a cable connection.

11. The system of claim 9 wherein each of the first and second receiver units are configured for bi-directional communication.

12. The system of claim 1 wherein the time information includes a beginning time and an end time of the inactive state.

13. A method of analyte monitoring, comprising:
transmitting a plurality of signals associated with detected analyte levels;
receiving a first portion of the plurality of signals at a first remote location;
receiving a second portion of the plurality of signals at a second remote location at least during an inactive state of the first remote location; and
storing time information associated with the inactive state at the first remote location.

14. The method of claim 13 further including the step of transmitting the second portion of the plurality of signals from the second remote location to the first remote location.

15. The method of claim 13 further including the step of storing the plurality of signals.

16. The method of claim 13 further including the step of displaying at least a portion of the plurality of signals.

17. The method of claim 13 wherein the time information includes a beginning time and an end time of the inactive state.

18. The method of claim 13 wherein the first and second portions of the plurality of signals are substantially non-overlapping.

19. A method of analyte monitoring, comprising:
retrieving a time information associated with an inactive state of a primary receiver unit;
transmitting the retrieved time information from the primary receiver unit to a secondary receiver unit; and
receiving one or more signals from the secondary receiver unit with the primary receiver unit, each signal associated with a monitored analyte level corresponding to the time information.

20. The method of claim 19 wherein the time information includes a beginning time and an end time of the inactive state.

21. The method of claim 19 further including the step of storing the received one or more signals in the primary receiver unit.

* * * * *

UNITED STATES PATENT AND TRADEMARK OFFICE
CERTIFICATE OF CORRECTION

| | | |
|---|---|---|
| PATENT NO. | : 7,801,582 B2 | |
| APPLICATION NO. | : 11/396181 | |
| DATED | : September 21, 2010 | |
| INVENTOR(S) | : Thomas A. Peyser | |

It is certified that error appears in the above-identified patent and that said Letters Patent is hereby corrected as shown below:

On the Title Page, item (57) Abstract, replace "configured with a limited functions" with --configured with limited functions--.

In the Drawings,
Sheet 1, Fig. 1, "SENSOR UNIT" in the box labeled 101 should be replaced with --"SENSOR"--.
Sheet 4, Fig. 5, the reference numeral 530 after "Receive transmitter unit data from secondary receiver unit associated with the time information" should be replaced with --540--.

In the Specification,
Column 2, line 35, replace "analyte monitoring system may" with --analyte monitoring system 100 may--.
Column 2, line 54, replace "data processing terminal in" with --data processing terminal 105 in--.
Column 2, line 56, replace "communication link 103 which" with --communication link which--.
Column 4, lines 46, 48, 49, 57 delete the reference numeral "103".
Column 4, line 54, replace "receiver 103" with --receiver 104--.
Column 4, lines 58-59, replace "Bluetooth" with --Bluetooth®--.
Column 4, line 62, replace "HIPPA" with --HIPAA--.
Column 5, line 11, replace "sensor unit 201" with --sensor 101--.
Column 6, line 36, replace "also shown is a" with --a--.
Column 6, lines 36-37, replace "leak detection circuit 214" with --leak detection circuit (not shown) is--.
Column 6, line 37, replace "guard electrode (G) 211" with --guard contact (G) 211--.
Column 6, line 40, delete reference numeral "214".
Column 7, line 45, replace "section 104" with --section 309--.
Column 8, line 31, replace "Bluetooth" with --Bluetooth®--.
Column 8, line 38, replace "both primary" with --both the primary--.
Column 8, line 62, replace "transmitter unit 104" with --transmitter unit 102--.
Column 10, line 5, replace "unit 520" with --unit 104--.
Column 10, line 16, replace "secondary receiver unit 104" with --secondary receiver unit 106--.

Signed and Sealed this
Fifth Day of July, 2016

Michelle K. Lee
*Director of the United States Patent and Trademark Office*

Column 10, line 33, replace "range with" with --range) with--.
Column 10, line 41, replace "102 to monitor" with --102 may monitor--.
Column 11, line 16, replace "Bluetooth" with --Bluetooth®--.

In the Claims,
Column 12, line 6, in claim 1, replace "sensor;" with --sensor,--.